US010773083B2

(12) United States Patent
Greenberg et al.

(10) Patent No.: US 10,773,083 B2
(45) Date of Patent: *Sep. 15, 2020

(54) METHODS AND SYSTEMS FOR DETECTING OBSTACLES FOR A VISUAL PROSTHESIS

(71) Applicant: Second Sight Medical Products, Inc., San Fernando, CA (US)

(72) Inventors: Robert J. Greenberg, Los Angeles, CA (US); Arup Roy, Valencia, CA (US); Avraham I Caspi, Rehovot (IL); Uday Patel, Los Angeles, CA (US); Mark D Welch, Saugus, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 79 days.

This patent is subject to a terminal disclaimer.

(21) Appl. No.: 14/854,916

(22) Filed: Sep. 15, 2015

(65) Prior Publication Data

US 2016/0317811 A1    Nov. 3, 2016

Related U.S. Application Data

(60) Provisional application No. 62/050,615, filed on Sep. 15, 2014.

(51) Int. Cl.
*A61N 1/36* (2006.01)
*H04N 13/128* (2018.01)
(Continued)

(52) U.S. Cl.
CPC ....... *A61N 1/36046* (2013.01); *A61N 1/0543* (2013.01); *G06K 9/00671* (2013.01);
(Continued)

(58) Field of Classification Search
CPC ............ A61N 1/36046; A61N 1/0543; H04N 13/0239; H04N 13/0022; H04N 5/2252;
(Continued)

(56) References Cited

U.S. PATENT DOCUMENTS

| 4,573,481 A | 3/1986 | Bullara |
| 4,628,933 A | 12/1986 | Michelson |

(Continued)

FOREIGN PATENT DOCUMENTS

| WO | WO 2008/109771 A2 | 9/2008 |
| WO | WO 2013/029097 A2 | 3/2013 |

*Primary Examiner* — Michael W Kahelin
(74) *Attorney, Agent, or Firm* — Scott Dunbar

(57) ABSTRACT

Systems and methods for detecting and displaying obstacles to visually impaired persons are disclosed. Images from a captured scene are analyzed to detect obstacles. A V-Disparity algorithm is employed to detect the ground plane and remove it from the images, thereby enhancing the capacity of retinal implants to display only obstacles. The system includes cameras to capture images; a processor with memory to detect obstacles in the captured images, to remove a ground plane, and to calculate a map of pixels representing the obstacles; and a retinal implant configured to receive the map of pixels and display the obstacles to a system user by electrically stimulating retinal nerves. The method includes synchronizing captured images and calculating a disparity map between the captured images to detect obstacles and remove a ground plane from processed images. A map of pixels representing the obstacle is transmitted to a retinal implant. Depth information may derive from stereo cameras, a time of flight camera or a structured light camera.

8 Claims, 19 Drawing Sheets

(51) Int. Cl.
　　　*G06K 9/00*　　　(2006.01)
　　　*G09B 21/00*　　(2006.01)
　　　*A61N 1/05*　　　(2006.01)
　　　*H04N 5/225*　　(2006.01)
　　　*H04N 13/00*　　(2018.01)

(52) U.S. Cl.
　　　CPC ....... *G06K 9/00805* (2013.01); *G09B 21/008* (2013.01); *H04N 5/2252* (2013.01); *H04N 13/128* (2018.05); *H04N 2013/0081* (2013.01)

(58) Field of Classification Search
　　　CPC ....... H04N 2013/0081; G06K 9/00671; G06K 9/00805; G09B 21/008
　　　See application file for complete search history.

(56) References Cited

U.S. PATENT DOCUMENTS

| | | | |
|---|---|---|---|
| 4,837,049 A | 6/1989 | Byers et al. | |
| 5,109,844 A | 5/1992 | de Juan, Jr. et al. | |
| 5,215,088 A | 6/1993 | Normann et al. | |
| 5,935,155 A | 8/1999 | Humayun et al. | |
| 6,400,989 B1 | 6/2002 | Eckmiller | |
| 6,458,157 B1 | 10/2002 | Suaning | |
| 2013/0012156 A1 | 5/2013 | Barnum et al. | |
| 2013/0121562 A1* | 5/2013 | Barnum | G06T 7/0075 382/154 |
| 2013/0128001 A1 | 5/2013 | You et al. | |
| 2014/0375782 A1* | 12/2014 | Chichilnisky | G06K 9/00671 348/62 |
| 2016/0325096 A1* | 11/2016 | Lui | A61N 1/36046 |

* cited by examiner

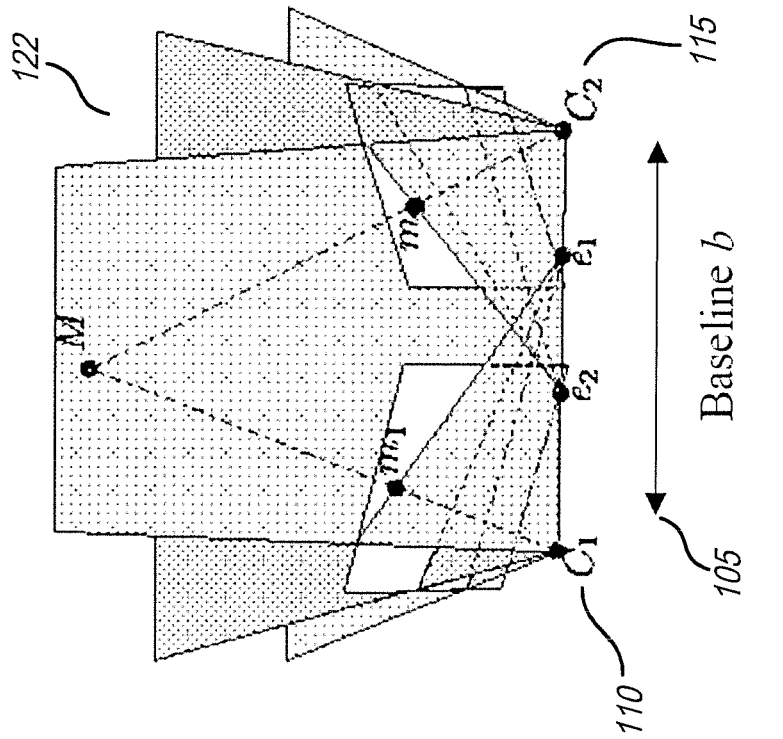
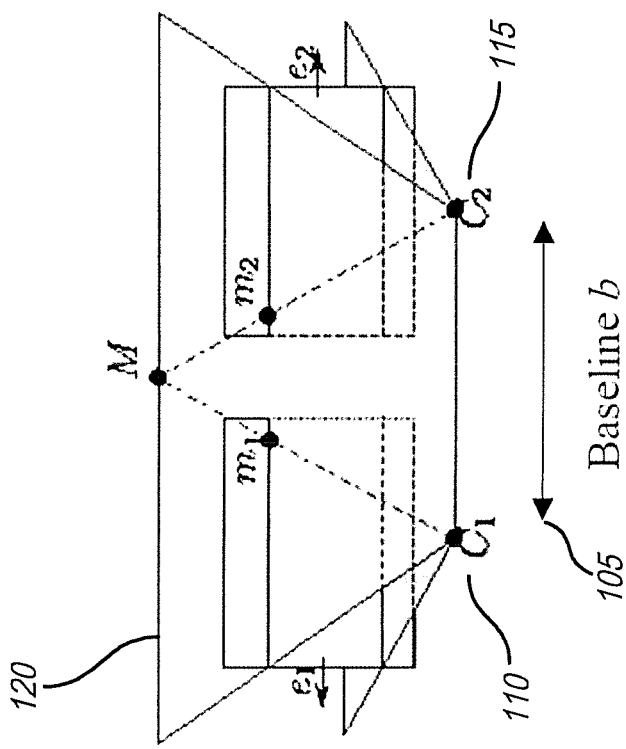
FIG. 1B
FIG. 1A

METHODS AND SYSTEMS FOR DETECTING OBSTACLES FOR A VISUAL PROSTHESIS

CROSS REFERENCE TO RELATED APPLICATIONS

This application claims priority to and incorporates by reference U.S. Provisional Application 62/050,615, filed Sep. 15, 2014, for Bilateral Visual Prosthesis and Depth Sensor.

BACKGROUND OF THE INVENTION

The present disclosure relates to visual prosthesis. More particularly, it relates to methods and systems for detecting obstacles for visual prosthesis.

SUMMARY

In a first aspect of the disclosure, a system to detect and display obstacles is described, the system comprising two or more cameras configured to capture images; a processor configured to detect obstacles based on the captured images, to remove a ground plane, and to calculate a map of pixels representing the obstacles; a memory configured to store data processed by the processor; and a retinal implant configured to receive the map of pixels from the processor and display the obstacles to a system user by electrically stimulating retinal nerves.

In another aspect of the disclosure, a method is provided to detect and display obstacles with the system in accordance with the current invention. The method includes capturing images with the two or more cameras and synchronizing the captured images with a processor operably connected to a memory configured to store data processed by the processor. The present method further includes using the processor for calculating a disparity map between the captured images and detecting the ground plane based on the disparity map. The processor generates a processed image representative of a view in front of the system user, based on the captured images and on the disparity map. The processor then removes the ground plane from the processed image and generates a map of pixels (data points) representing detected obstacles and transmits the map of pixels to a retinal implant. The map of pixels is displayed to the system user by electrically stimulating the retinal nerves through the retinal implant.

In a further aspect of the present invention, the processor detects the ground plane based on a V-Disparity algorithm. In addition, timestamps associated with the captured images may be used by the processor for the synchronizing the captured images. Generating the map of pixels may comprise increasing a brightness of the pixels based on a distance from the user of the system, wherein increasing a brightness of the pixels is nonlinear with respect to the distance. Also, generating a processed image may comprise calculating a depth map based on the disparity map.

In another aspect of the disclosure depth information may derive from stereo cameras, a time of flight camera or a structured light camera.

Other features and advantages of the invention will become apparent from the following detailed description, taken in conjunction with the accompanying drawings, which illustrate, by way of example, the features of the invention

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIG. 1A shows a parallel camera configuration.
FIG. 1B shows a verged camera configuration.
FIGS. 19-1, 19-2, 19-3 and 19-4 show an exemplary embodiment of a video processing unit.
FIG. 19-1 should be viewed at the left of FIG. 19-2.
FIG. 19-3 should be viewed at the left of FIG. 19-4.
FIGS. 19-1 and 19-2 should be viewed on top of FIGS. 19-3 and 19-4.

DETAILED DESCRIPTION

Figure 2:
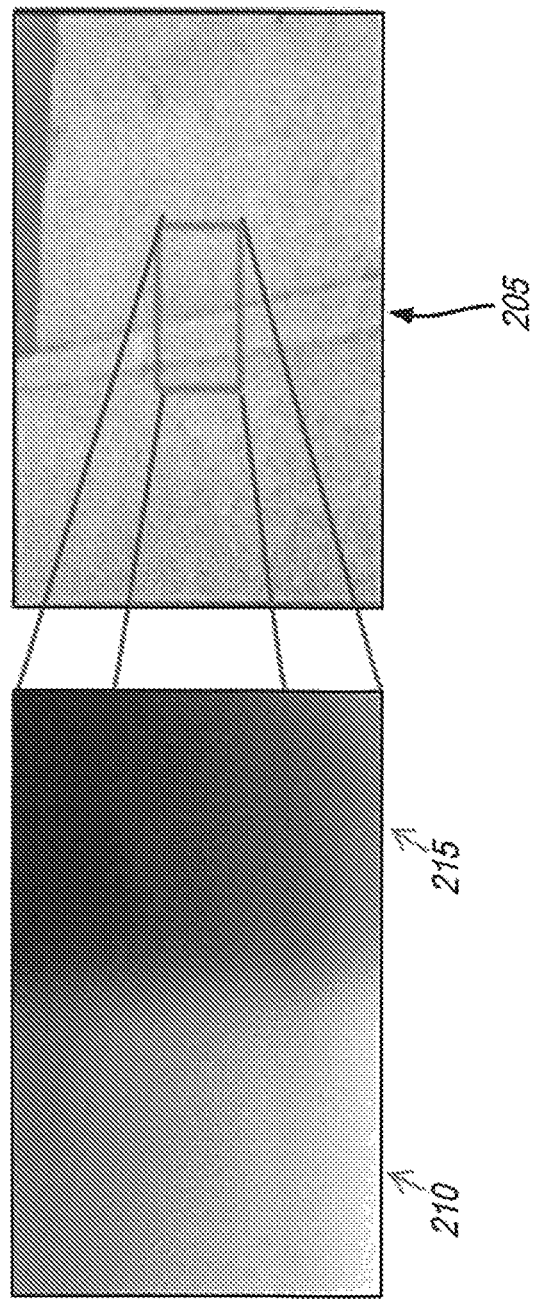
FIGS. 2-3 illustrate examples of detection of obstacles.

The present disclosure relates to methods and systems that analyze the scene captured by two or more cameras, in order to process the scene and relay visual information to visually impaired human beings. The visual information is relayed to a prosthetic device, for example implanted in a human eye or visual cortex. The visual implant can be surgically implanted in the retina or visual cortex of the brain and, depending on the number of electrodes, can provide electrical signals that are interpreted by a person as a pixelated image of the physical scene in front of the person. For example, if the implant has a defined number of electrodes, a corresponding number of pixels (data points or elements in the view) may be visualized to provide information on the visible scene. Since, in some embodiments, the number of electrodes is insufficient to provide information on every detail of the scene, an algorithm (a procedure programmed in software executed by a processor having memory) can determine what information should be displayed by the implanted device. For example, the algorithm may detect obstacles in the walking path of the person implanted with the visual prosthesis. The algorithm may determine the most efficient or optimal way to display the obstacle information to the implant.

Obstacle detection is an essential functionality for any visual prosthesis device. Currently, several retinal prosthesis devices stimulate the retina based on the brightness of the object in the receptive field of the implant. Sighted individuals detect obstacles by using higher level processing to create the shape of the object based on brightness and depth. Retinal prosthesis devices do not provide generally depth information. Moreover, due to the limited resolution, field of view, and dynamic range of the prosthesis, it can be difficult to detect an obstacle, unless the color brightness and/or texture of the obstacle stand out from the background.

The present disclosure describes methods and systems that incorporate an algorithm developed in the field of intelligent and autonomous vehicles, called the V-Disparity algorithm, to detect objects on the road. The V-Disparity algorithm uses 2D fitting to detect the ground. For each image analyzed by the V-Disparity algorithm, each pixel that is removed from the ground is tagged as an obstacle. In other words, the V-Disparity algorithm detects pixels that do not belong to the ground and categorizes them as an obstacle.

A different method for ground detection is by plane fitting in 3D which requires a significant amount of processing power and cannot therefore be implemented in real-time devices with wearable electronics, due to limited processing power of such devices. Therefore, the V-Disparity algorithm presents a great improvement over other methods as it uses 2D fitting, thus requiring less processing power.

The systems of the present disclosure employ at least two small video cameras, which can be worn by an individual. For example, the cameras may be mounted to a pair of glasses. By providing at least two cameras, stereoscopic detection can be employed. In some embodiments, two cameras are used. Images from the two cameras are transmitted to a processor. The processor may be worn by the individual, and the cameras may be connected to the processor by wires or wirelessly. The processor can calculate a disparity map based on the data from the cameras. The disparity map may contain information on the difference between the left view and the right view, or the different views from the two or more cameras. For example, the disparity map may consist of an image that records, for each pixel, a disparity, or difference, between pixel positions of two images. For example, the difference may be in the pixel position for a left image and a right image. The disparity map can then be transmitted to the ground detection algorithm in the processor. The ground detection algorithm can detect the ground level, ground plane or ground surface, distinguishing it from the remaining part of the viewable scene. The disparity map can be calculated, for example, by measuring the difference in position between the same object in the left and right image. The distance for each pixel can form a map, called a disparity map.

In some embodiments, each pixel in the view that is not on the line of the ground in the V-Disparity algorithm is tagged as an obstacle. After the ground detection algorithm has been applied and the ground level has been detected, a sub-sampling algorithm can build a stimulation map for the implanted electrodes array. This is due to the fact that the implanted array has a limited amount of pixels, therefore the view has to be sub-sampled to the correct resolution of the implanted array of electrodes. In some embodiments, the sub-sampled image contains information only on items that are removed from the ground.

In other words, by removing pixels associated with the ground plane, the limited number of pixels available in the implant can be employed to visualize information only on obstacles, that is, objects which have a height higher than the ground level.

The V-Disparity algorithm has been disclosed, for example, in Labayrade, R., Aubert, D., Tarel, J.-P.: Real Time Obstacle Detection on Non Flat Road Geometry through "VDisparity" Representation. 2002, IEEE Intelligent Vehicle Symposium, 646-651, Versailles, France, 18-20 Jun. 2002, the disclosure of which is incorporated by reference herein in its entirety. The V-Disparity algorithm is also described in U.S. Pat. No. 8,923,605, Dec. 30, 2014, "METHODS AND SYSTEM FOR DETECTING OBJECT ON A ROAD", and U.S. Pat. No. 8,861,791, Oct. 14, 2014, "METHOD AND DEVICE FOR DETECTING ROAD REGION AS WELL AS METHOD AND DEVICE FOR DETECTING ROAD LINE", the disclosure of both of which is incorporated herein by reference in its entirety.

U.S. Pat. No. 8,923,605 describes the algorithm in this way: "The V-disparity algorithm may simplify a division process of an obstacle and a road surface. In a V-disparity image, V corresponds to the vertical coordinates in the image coordinate system of a disparity map. In a V-disparity domain, a longitudinal section of a road surface may be described as a piecewise linear curve, and an obstacle in a vertical plane may be projected as a vertical line. As a result, an extraction of a road surface and an obstacle in a 3D disparity map may be simplified as a 2D (two-dimensional) line extraction in a V-disparity image. In this way, it is possible to recognize an obstacle in front of a vehicle, having a surface feature, for example, a passer-by, another vehicle, or a wall. In addition, this kind of algorithm is not sensitive to interference such as lighting, shadows, or the like; consequently the algorithm is suitable for obstacle recognition for an intelligent vehicle, under a complex background. In particular, a V-disparity recognition process based on the two eyes of a human being mainly comprises three contents, namely, creating a V-disparity image, extracting a road surface, and extracting at least one vertical line representing an object on the road surface."

The present disclosure describes methods through which the V-Disparity algorithm can be integrated in a visual prosthesis device. Theoretically, the baseline between cameras for the V-Disparity algorithm has to be parallel to the ground. However, the present disclosure describes that the parameters of the V-Disparity algorithm can be adjusted in order to accommodate the error due to the tilt of the camera in a head mounted configuration.

In some embodiments, the implanted device may therefore display information on obstacles that surround the individual wearing the implant. For example, there may be a streetlight in the walkway, and the individual may be walking towards it. Alternatively, a hat rack may be in a hallway of a house. In both occasions, the algorithm may detect the ground level, detect the tall obstacle (streetlight or hat rack) and display in the electrode array of the implant a single vertical line with bright pixels. The vertical line can then be interpreted by the wearer as a vertical obstacle. This also applies to lower obstacles like a curb, or other trip hazard. Curbs, in addition to presenting a trip hazard, may be useful for orientation as a guide to follow. Other obstacles may be present in the background, for example a chest of drawers. This obstacle may be displayed as a rhomboid. In some embodiments, the obstacles in the background may be displayed with pixels that have a lower brightness compared to the obstacles closer to the individual. For example, the chest of drawers may be displayed with pixels of a lower intensity than the hat rack. In such a way, the individual can navigate the scene with more ease due to the depth information of various obstacles.

The methods described therein, therefore, use three-dimensional information detected in the scene, and can provide improved information to the individual wearing the implant, compared to other approaches. For example, another approach is based on a luminosity representation. This approach represents objects based on the reflected light. However, this can introduce a lack of clarity to the wearer that renders it difficult navigating an unfamiliar scene if the scene has regions with different illumination (for example due to a bright window).

Stereo cameras as used in the present disclosure are passive sensors that can acquire images and estimate corresponding dense (pixelwise) depth maps at a near real-time frame rate. In some embodiments, two cameras are used. In other embodiments systems composed of three cameras can be used. With two cameras, the principle is to mimic natural perception of depth as in the human vision, associated with the simultaneous perception of two point of view (one for each eye). Output of the system is a dense estimation of depth information of the scene, thus to each captured image pixel, there is an associated estimated depth value representing the distance from the viewer to the scene entities. In some embodiments, the use of three cameras can help extend the range due to several options available for baselines between cameras.

Such a system is interesting in regard to the possibility of integration with implantable devices. Indeed, cameras can be easily embedded in the glasses frame, for example. As the cameras are passive and do not rely on emissive technology such as an infrared projector, they mainly only require additional processing power, and do not consume great amount of power, an advantage considering that the individual is carrying the battery that is powering the system.

Figures 1, 19:
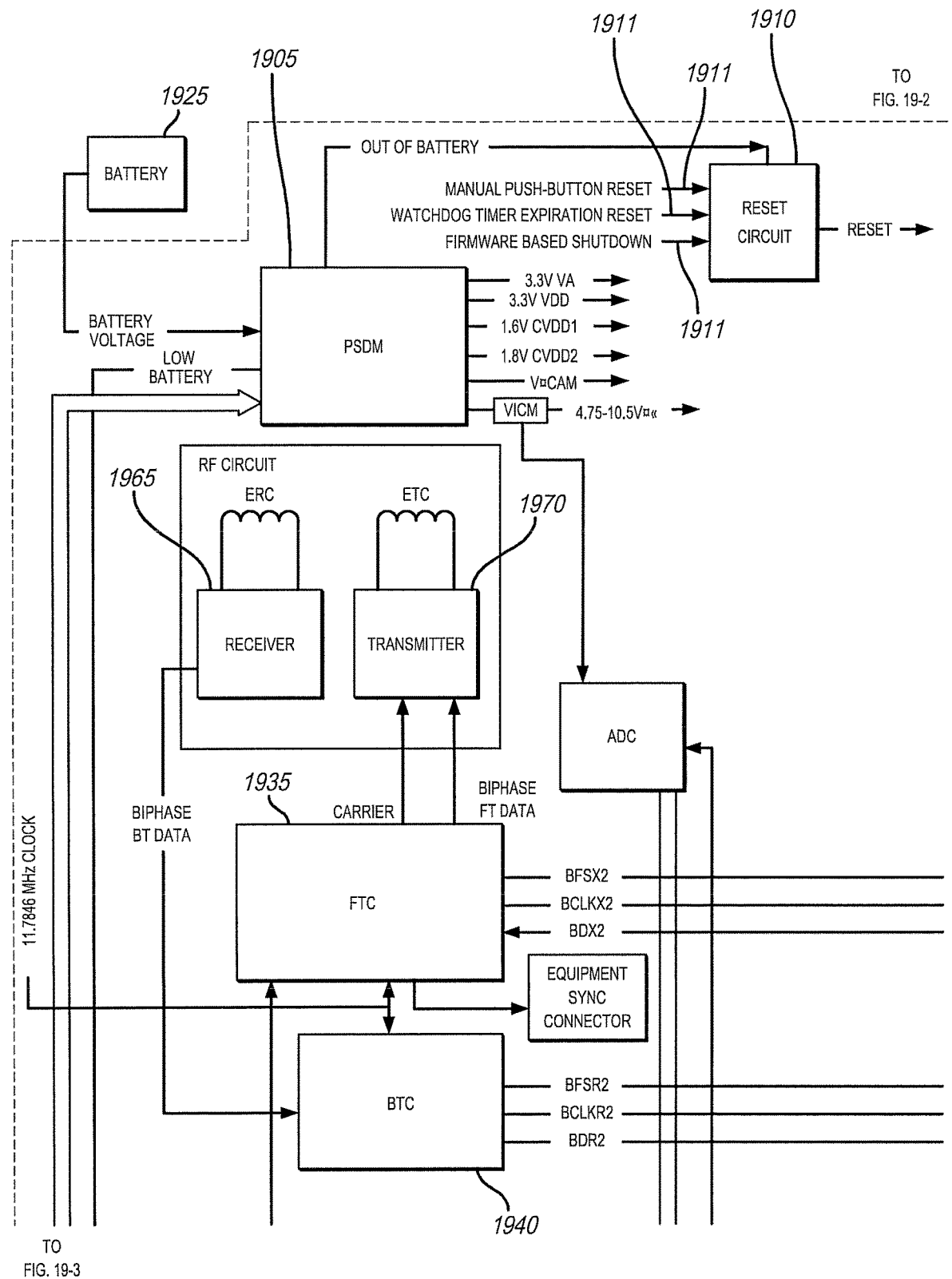
Figures 2, 19:
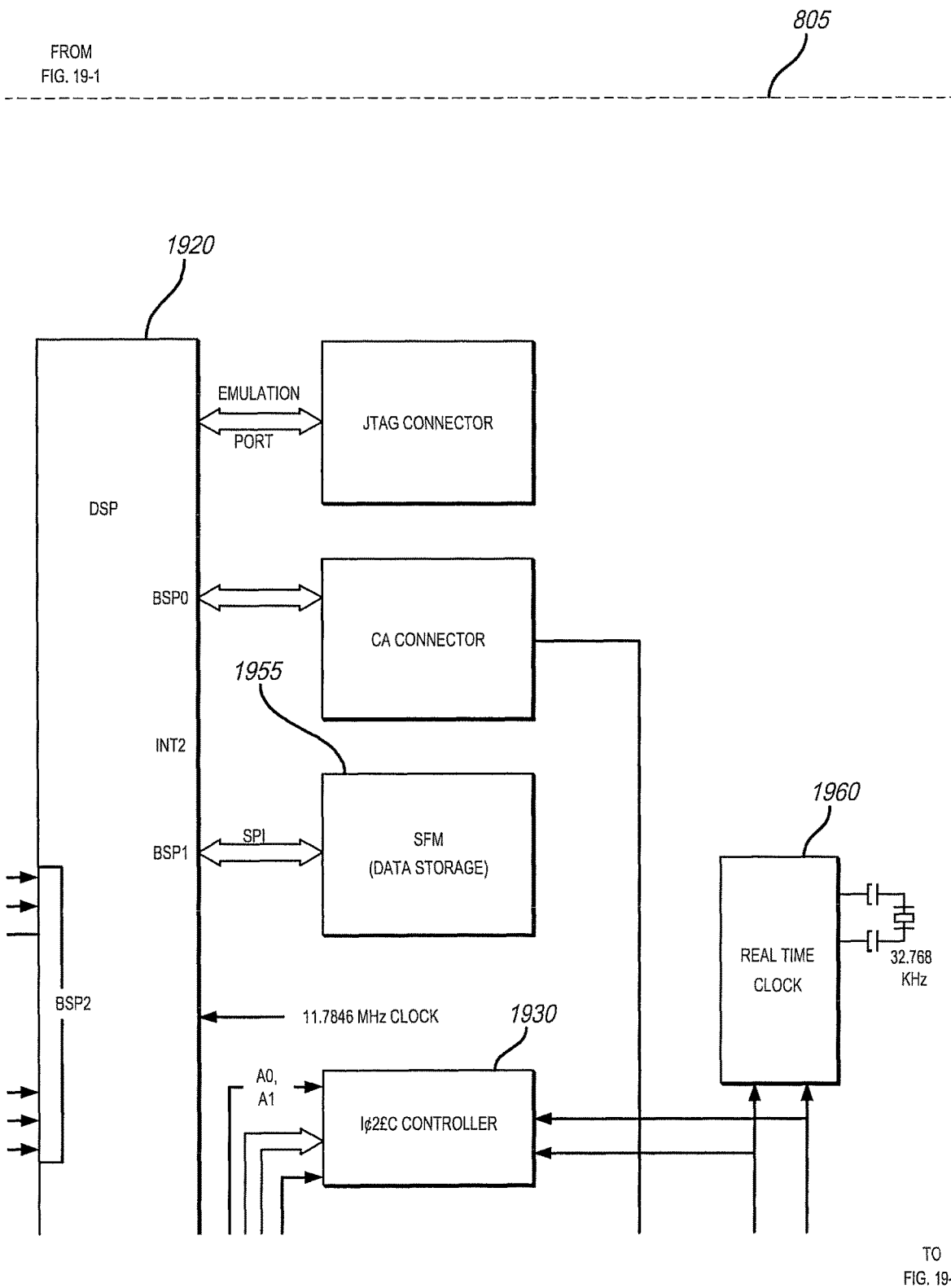
Figures 3, 19:
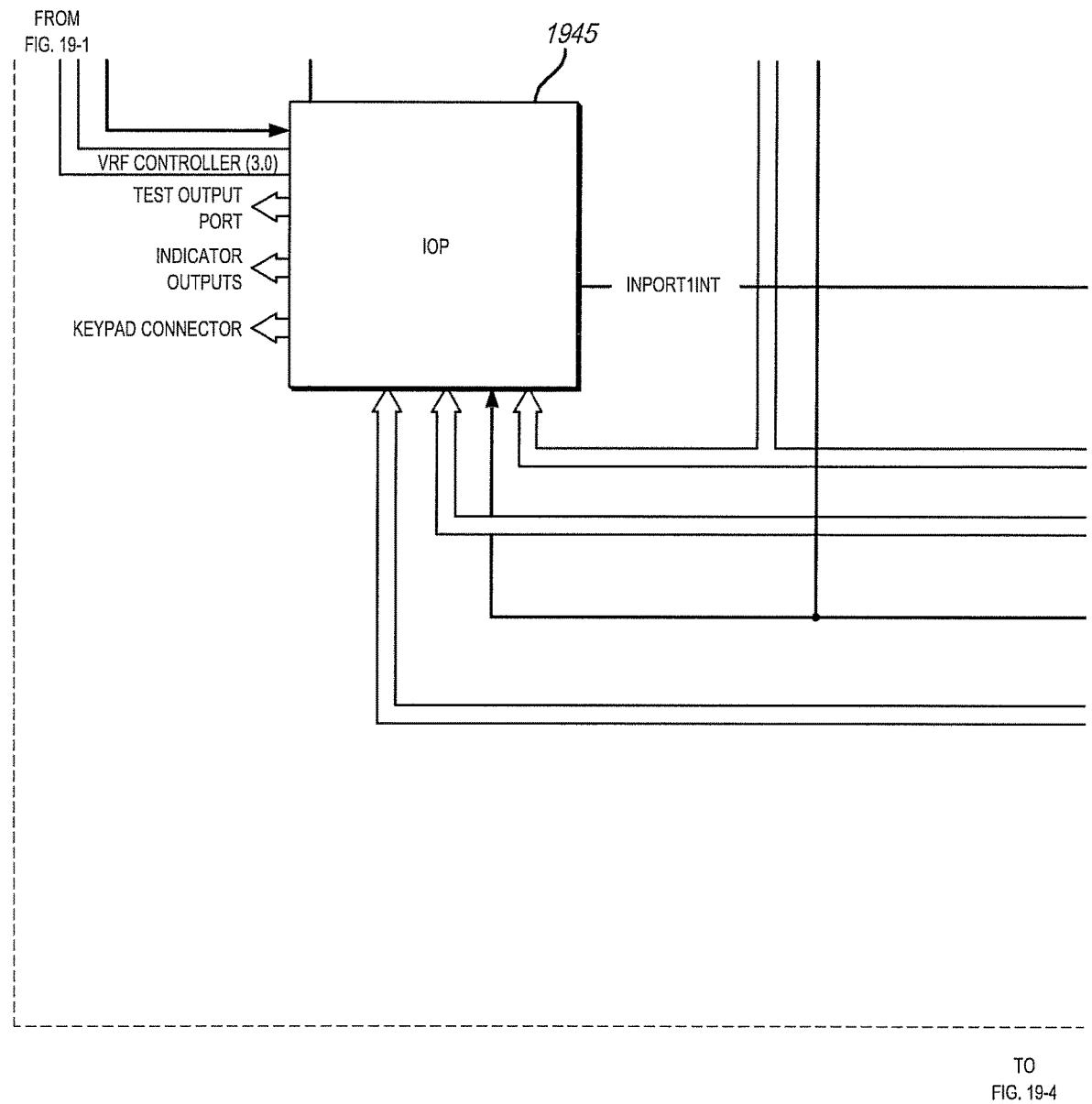
Figures 4, 19:
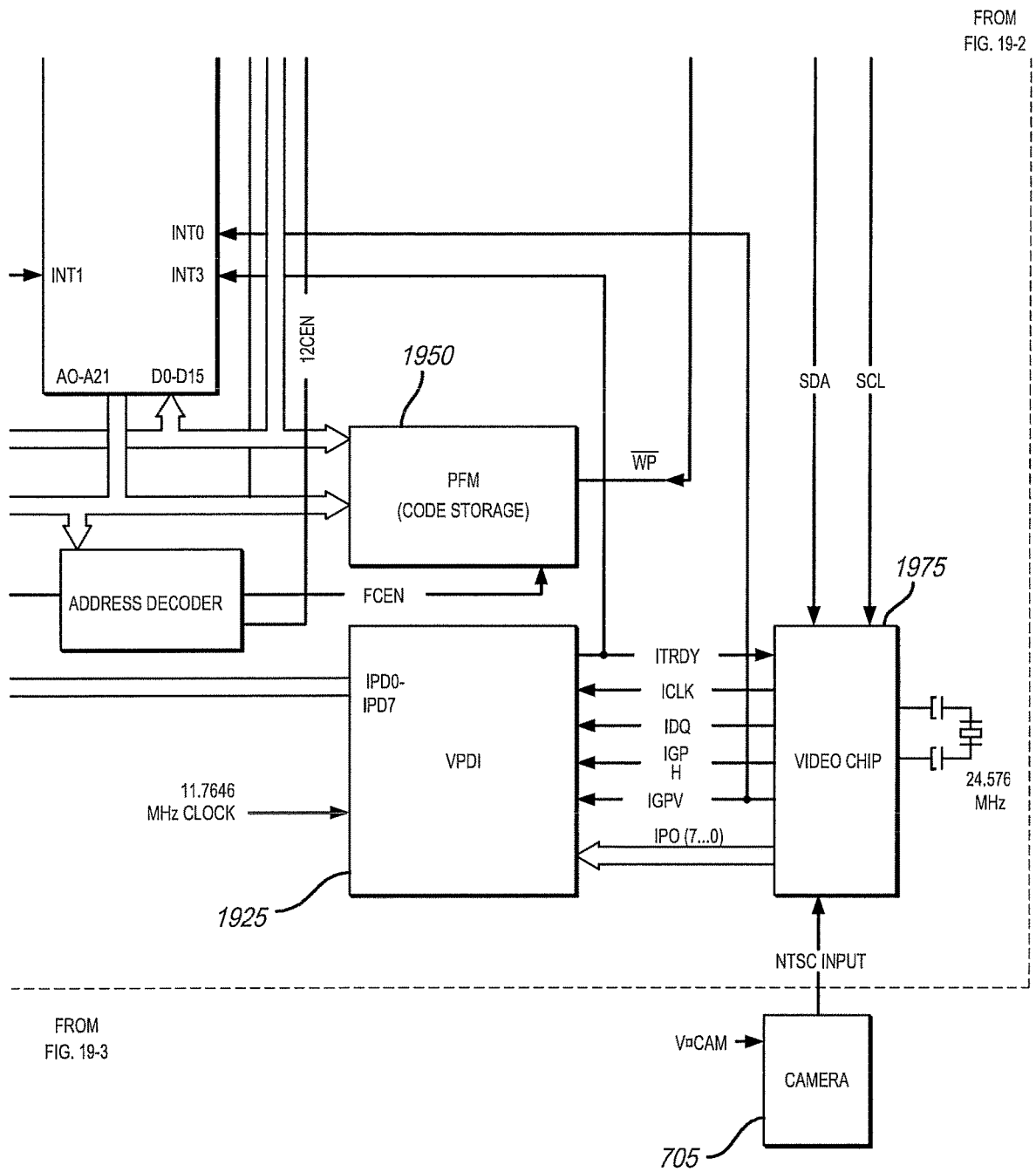

The algorithm that processes the cameras' information may employ different parameters. For example, as illustrated in FIG. 1, the baseline parameter (105) represents the distance between the two cameras (110, 115). The cameras orientation may be parallel (120) or verged (122). In FIG. 1, m (m1 and m2 for the two cameras C1 and C2) is the projection of the target M on the focal plane which is flipped forward, and e (e1 and e2 for the two cameras C1 and C2) is the transformation from verged to parallel axis in order to compute the range, epipolar correction as explained below.

Verged cameras are oriented in order to point to a fixed (maximum) distance in front of the system. Parallel cameras optical axes are set as parallel as possible. In some embodiments, only parallel cameras are used as this arrangement can simplify search efficiency for stereo matching. Camera centers c1 and c2 are separated by a distance b called baseline. Along with other parameters, such as the focal length of the lens, the baseline distance controls the value of the minimum distance that can be detected by the system.

Optics is an important factor in stereo vision systems, and the related parameter is the focal length. Reducing the focal length can allow a wider field of view (but a less precise image, if the resolution is maintained) thus allowing closer distances to be detected. Focal length and baseline values can be set accordingly to the desired arrangement.

In some embodiments of the present disclosure, stereo vision systems estimate the depth based on a triangulation method. Estimating the depth of an object requires that the same object points are found in the two images, left and right. The distance that separates the two projections of a same object, which is called disparity, is directly related to the depth value. The disparity search range is the maximum pixel distance (distance between elements in the captured images) between two points (elements in the captured images) within which the algorithm will operate. Because the range is proportional to the inverse of the disparity, the minimum depth that the system can detect is set by the maximal disparity.

The camera pair can also require synchronization: in order to perform the matching process under optimal conditions (when the two points of view are separated spatially not temporally), the cameras must capture the two frames simultaneously. For example, each frame from a camera may have a time stamp as metadata. Some cameras allow the use of an external trigger. Providing this signal to the two cameras allow the system to perform these synchronized captures. For example, a trigger signal may be delivered to the two cameras by an oscillator circuit. The trigger signal may be of any frequency, for example 20 or 30 Hz. The frequency of the trigger can be set in accordance with the required processing time. Synchronization may be carried out by reading the time stamps on each camera frame. Cameras may be dedicated machine vision cameras, or also webcams.

In some embodiments, an epipolar correction is applied to the images of the two cameras, so that the projection of an observed object point in the two cameras is separated only along the horizontal axis. As known to the person skilled in the art, epipolar geometry is the geometry of stereo vision, and epipolar correction is a known set of calculations that can be applied to stereo vision. Since the line of sight of each camera is distinct, a correction must be made to account for the geometry of the cameras.

The methods of the present disclosure describe how depth information, that is a distance from the individual wearing the implant, is calculated based on the disparity value between objects detected by the two cameras. The disparity value at each sub-sampled area in the image may correspond to a range of distances depending on the baseline and focal length of the two cameras. Once the baseline and focal length are set for the system, the algorithm can calculate distance to obstacles based on the disparity in each sub-sampled area in the image.

FIG. 2 illustrates an example of detection of an obstacle. The step on the curb (205) is detected and the algorithm interprets it as having a ground level (215) and a higher level (210). The higher level walking ground is depicted with bright pixels while the ground level is dark. For example, the algorithm may be configured to increase the brightness of pixels determined to be above ground, and subsequently the system may increase the current or voltage at the electrodes of the retinal implant in order to increase the brightness perceived by the system user in the retina.

Figure 3:
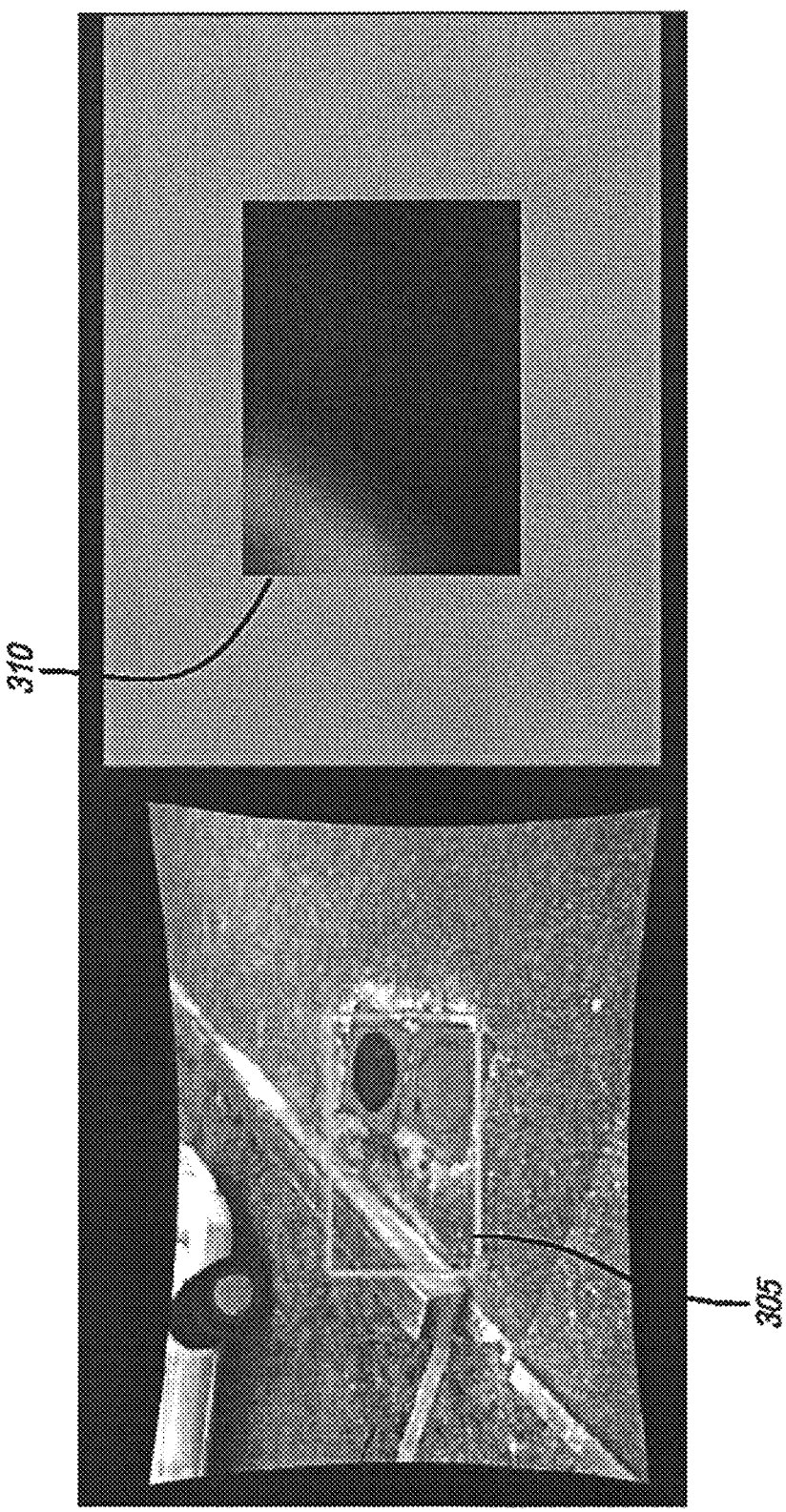

FIG. 3 illustrates a further example of detection of an obstacle. The short wall (305) is detected and illustrated as a white line (310), contrasted to the ground level which is dark. Other objects in the pictures are not detected as obstacles and do not clutter the view provided to the implant. In some embodiments, a low pass spatial filter, such as Gaussian smoothing may be used on the images together with the ground detection and removal algorithm.

Figure 4:
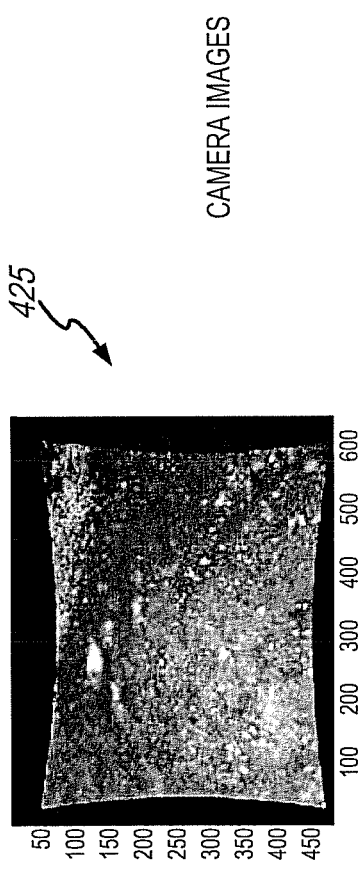
FIG. 4 illustrates an example of disparity images.
Figure 4:
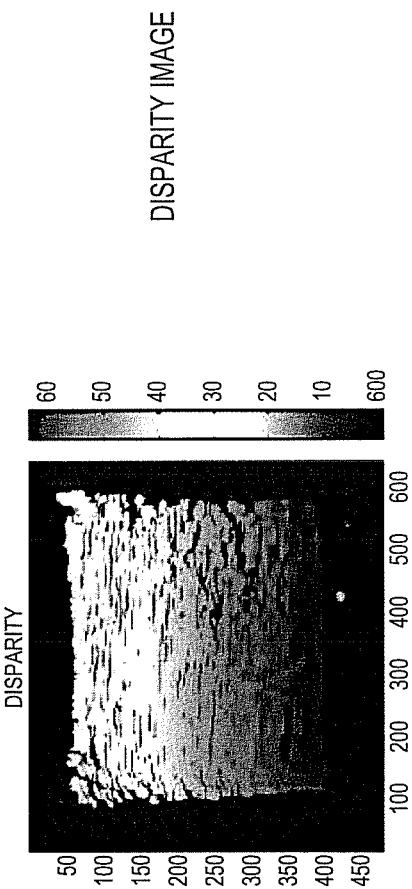

By processing 3D data it is possible to perform obstacles and ground plane detection. The method comprises the simplification of the scene representation, obtained by only transmitting pertinent information (obstacle positions, extents and distances) to the implantee. One technique for ground detection compatible with near real time processing is the V-Disparity algorithm. The V-Disparity technique is based on the following observation: in the camera image and disparity image, the pixels of the ground have 3D values that go progressively from a close distance (at the bottom of the image) to a far distance (at the horizon). Finding the ground plane is equivalent to finding a line in a specific representation that is called V-Disparity. A first step comprises estimating a disparity image. Disparity images constitute the input of the V-Disparity algorithm. In FIG. 4 two examples are illustrated: a disparity image with obstacles (405) and a disparity image without obstacles (410). Both are derived from corresponding image cameras (420, 425). V-Disparity representation is equivalent to a 2D histogram of the disparity. Each V-Disparity image line is the histogram of the disparity value found in the corresponding disparity image line.

In subsequent step, the line that represents the ground plane is detected by the algorithm. This can be done using line detection algorithm, such as Hough Transform. A binary image is calculated to emphasize the line corresponds to the ground. In a subsequent step, regions of the disparity image that do not contain the ground line are removed of any information, since it is not relevant to the ground detection. Further, the detected lines are compared with computer score values (threshold values), and the line that represents the ground is found. Applying a threshold based on the ground line allows the algorithm to divide the image in two regions, with elements that are below or above the threshold. Regions that are below the threshold are marked as ground, while regions of the image with a higher than threshold value are marked as obstacles.

In the case of an environment with many elements present in the vicinity, it is possible to filter the information on the basis of the distance and to present only entities contained in a restricted volume close to the subject. This should limit the attention effort required to decode the scene by presenting only relevant information for a safe travel. In order to simplify the representation for the user, an obstacle or other entity in the image map can be selected based on their distances from the user. The system will transmit to the visual prosthesis and the resulting stimulation of the retina (phosphine generation) only obstacles at a certain range of distances. For instance, objects presented in the scene representation can lie in the cylindrical volume defined by a minimum and maximal distance value. In some embodiments, obstacles which are closer can be represented by pixels with a higher brightness compared to pixels representing obstacles which are further away. Therefore, such a nonlinear mapping may be advantageous compared to a linear mapping that scales the brightness based on the distance, without emphasizing the closest objects.

Figure 5:
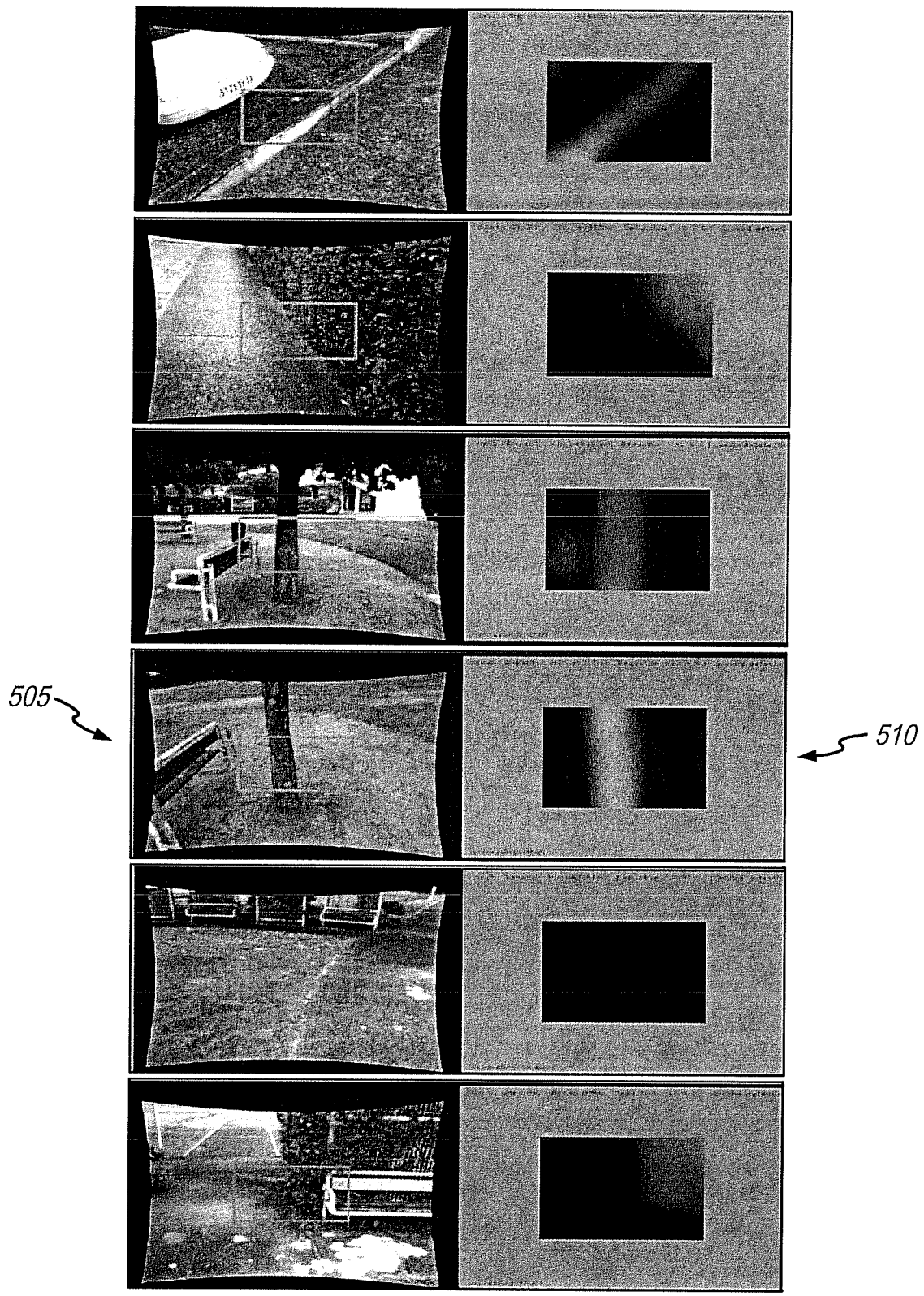
FIG. 5 illustrates examples of detection of ground level and obstacles.

FIG. 5 illustrates examples of detection of ground level and obstacles. For example, a tree (505) is detected, the corresponding ground level is detected and removed from the image, and only a vertical bright line of pixels is displayed (510).

In some embodiments, data from an accelerometer detecting acceleration and movement of the individual wearing the system could be integrated in the algorithm in order to improve detection and display of obstacles and scene information. By using an accelerometer, the performance of the methods of the present disclosure can improve especially in situations when the cameras horizontal axes are not parallel to the ground plane.

Figure 6:
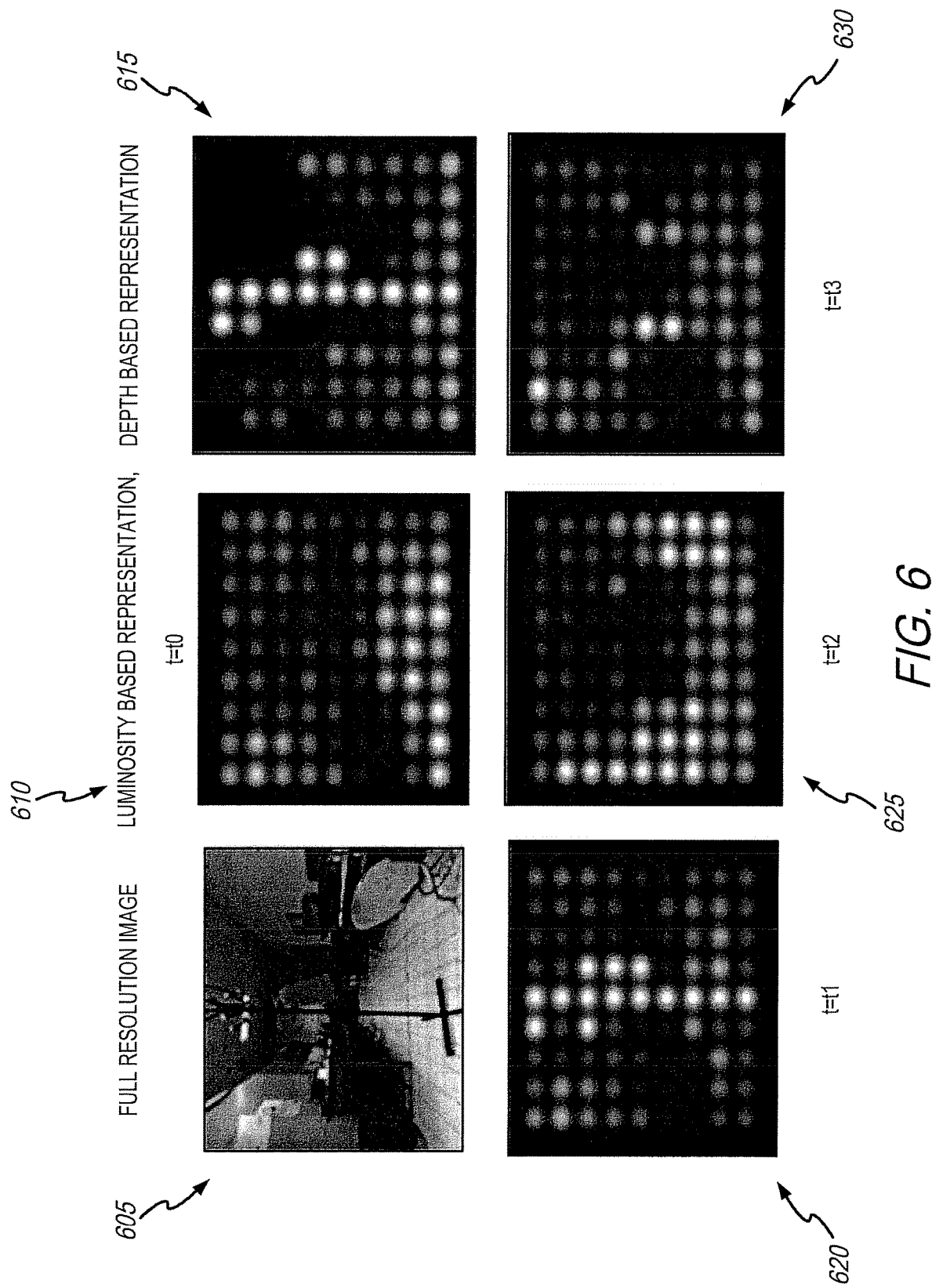
FIG. 6 illustrates an example of an obstacle detection and display in an exemplary array.

FIG. 6 illustrates an alternative embodiment of an obstacle detection in which depth is encoded differently, using cycle. At each time window different distances are presented. This is repeated in a cycle. An exemplary array of 9×9 pixels could be realized with an array of 9×9 implanted electrodes. In other embodiments, a higher number of electrodes may be used, for example 16×16 or 64×64. In FIG. 6, a vertical obstacle is illustrated (605). An algorithm only based on the luminosity of the scene objects (610) is not adequate to detecting the dark vertical obstacle closest to the viewer. However, a depth-based representation as described in the present disclosure is able to display a bright vertical line of bright pixels (615) alerting the wearer to the nearby vertical obstacle. A combination of luminosity and depth-based techniques can give a composite representation.

For example, FIG. 6 illustrates simulated prosthetic images obtained with a composite representation. The simulation images of FIG. 6 use Gaussian-shaped blobs to illustrate the stimulation level for each electrode site in the retina activated. Information for a safe navigation, such as the existence of the obstacle in the foreground of the image (605) is not accessible through the representation solely based on luminosity (610). However, it is possible to detect small objects when using temporal depth-based representation. The images in the bottom row of FIG. 6 illustrate different slices based on distances, each presented to the user at a different time t1 (620)<t2 (625)<t3 (630).

Figure 7:
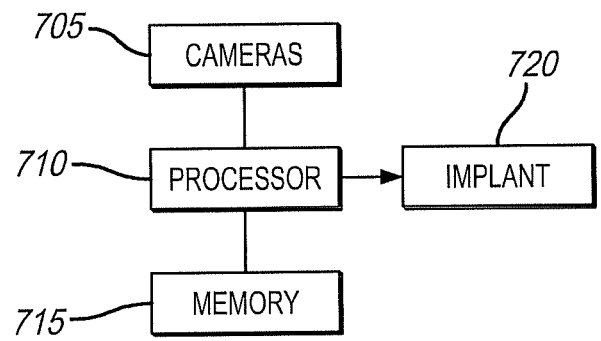
FIG. 7 illustrates an example of a system to detect obstacles.

FIG. 7 illustrates an example of a system to detect obstacles. A pair of cameras (705) worn by a user is connected to a processor (710). The processor (710) can apply the V-Disparity algorithm to detect the ground level from the images taken by the cameras. The processor can also use the output of the V-Disparity algorithm to generate an image where the ground level has been removed, and the closest obstacles are highlighted and displayed by bright pixels. This image is sent to the array of electrodes in the retinal implant (720). The processor is also connected to a memory (715) to store parameters and values calculated by the V-Disparity algorithm. For example, the processor may store disparity values in a first memory location, baseline and focal length parameters in a second memory location, and the pixel map representing the obstacles in a third memory location.

The incorporation of the V-Disparity algorithm with dual cameras is therefore aimed at biomedical implants, in particular with the detection and removal of the ground floor. The V-Disparity algorithm detects the ground floor and additional scripts, based on the V-Disparity algorithm, remove the ground floor from the actual vision pixels of the implant wearer.

Figure 9:
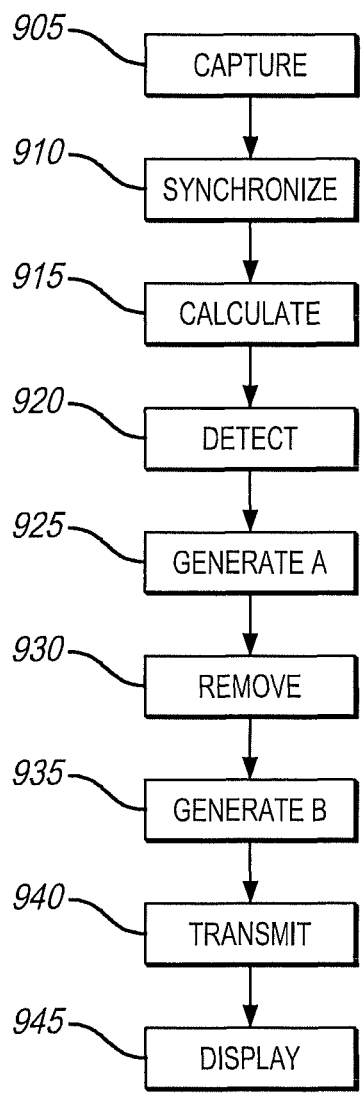
FIG. 9 depicts an exemplary embodiment of a method flowchart of an embodiment of the present disclosure.
Figure 10:
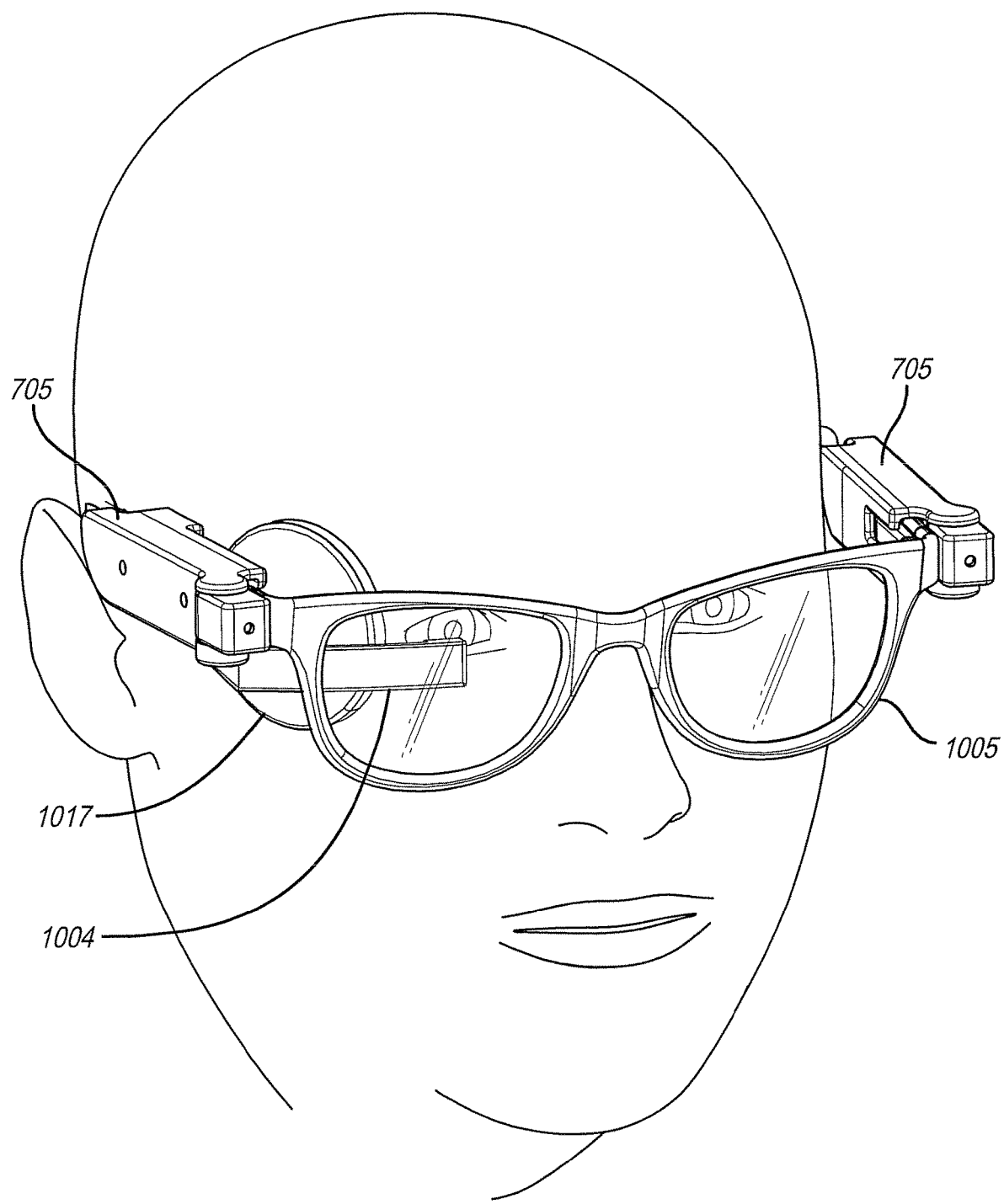
FIG. 10 is a perspective view of a person wearing bilateral glasses.
Figure 11:
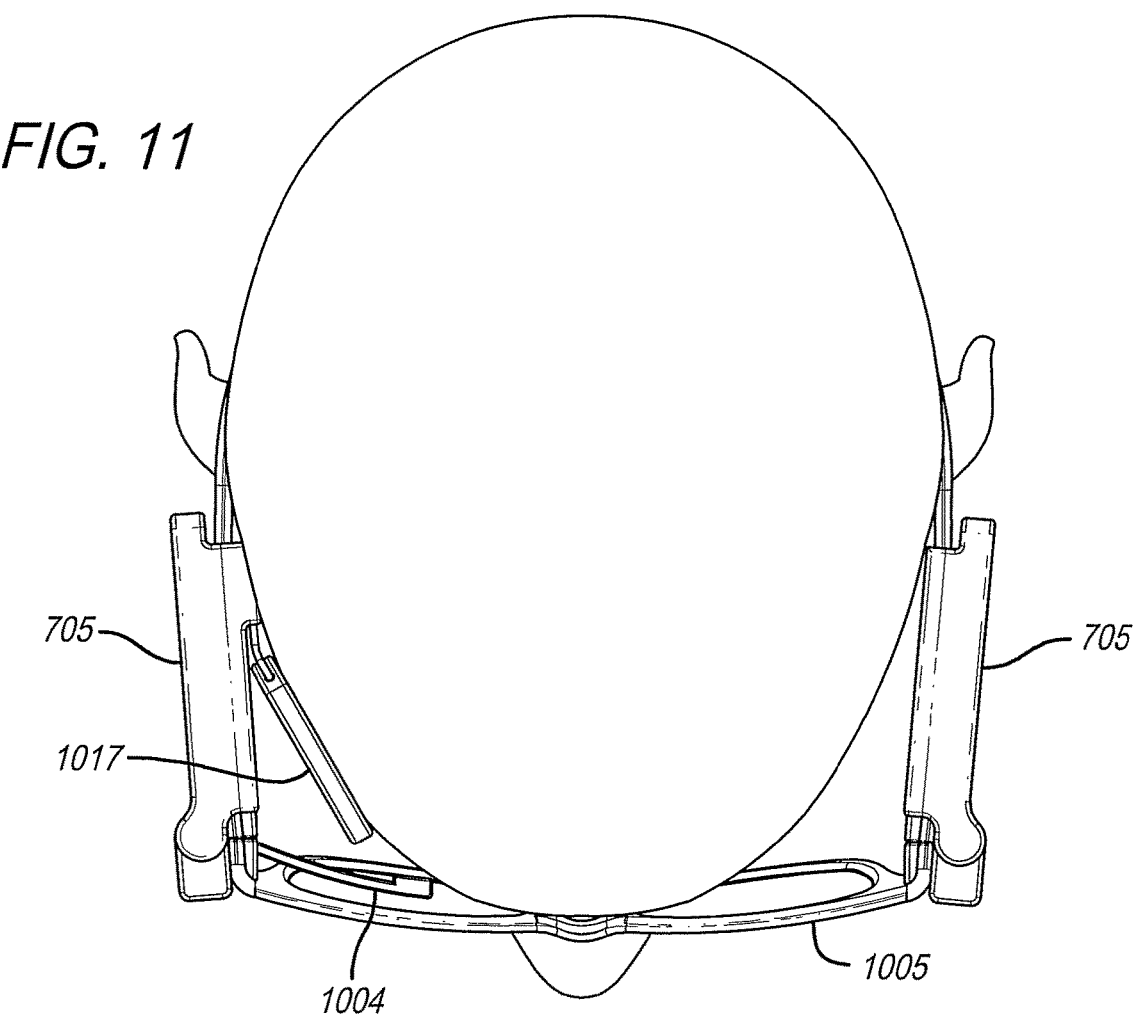
FIG. 11 is a top view of a person wearing bilateral glasses.
Figure 12:
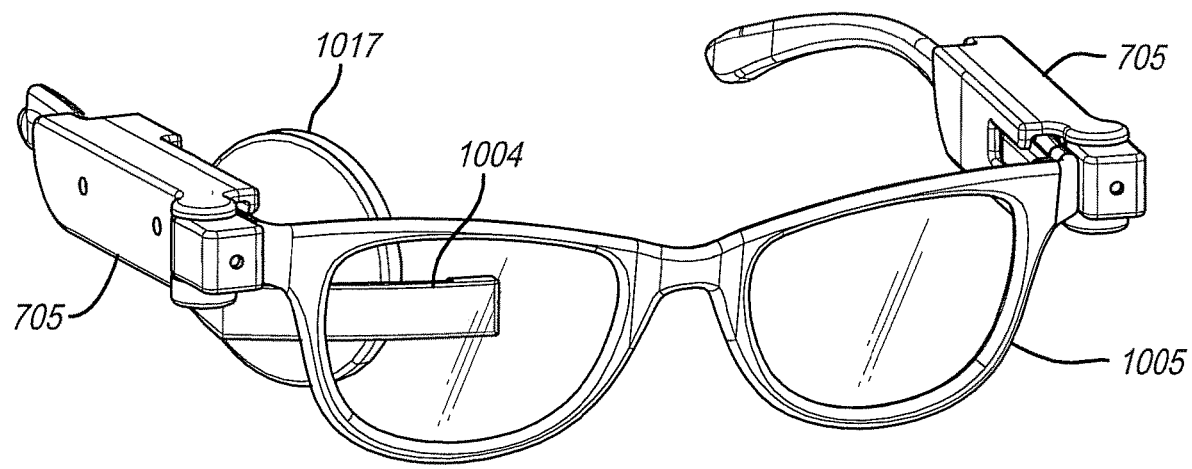
FIG. 12 is a perspective view of the bilateral glasses.
Figure 13:
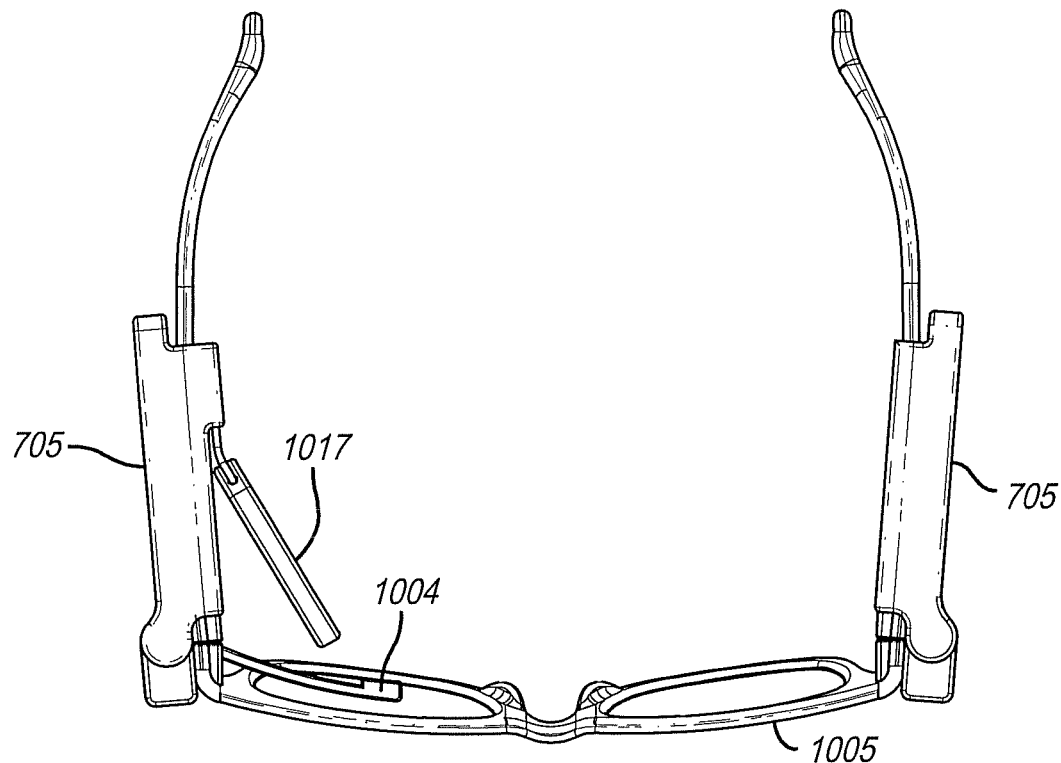
FIG. 13 is a top view of the bilateral glasses.
Figure 14:
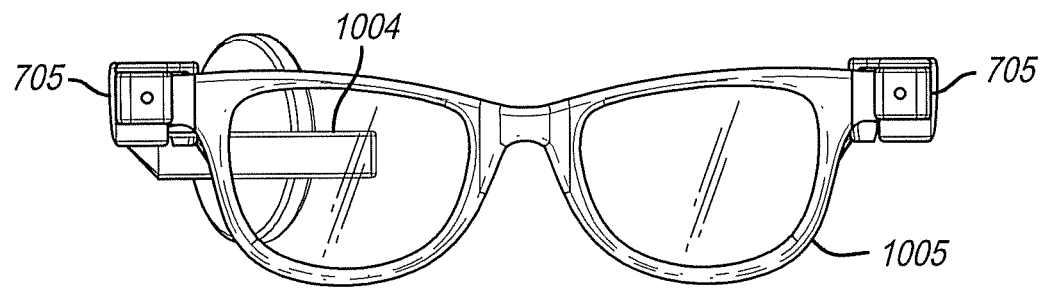
FIG. 14 is a front view of the bilateral glasses.

In some embodiments, a method to detect and display obstacles with the system of the present disclosure may comprise the following steps, as illustrated in FIG. 9. Capturing images with the two or more cameras (905); synchronizing, by the processor, the captured images (910); calculating, by the processor, a disparity map between the captured images (915); detecting, by the processor, the ground level based on the disparity map (920); generating, by the processor (Generate A), a processed image representative of a view in front of the system user, based on the captured images and on the disparity map (925); removing, by the processor, the ground level from the processed image (930); generating, by the processor (Generate B), the map of pixels representing the obstacles (935); transmitting the map of pixels to the retinal implant (940); and displaying the map of pixels to the system user by electrically stimulating the retinal nerves (945).

Figure 8:
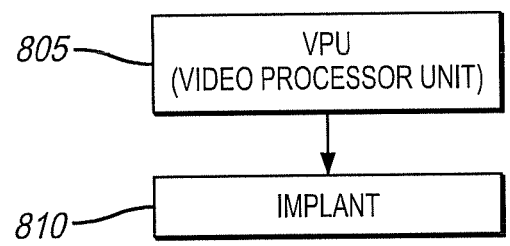
FIG. 8 depicts an exemplary embodiment of target hardware for implementation of an embodiment of the present disclosure.

FIG. 8 is an exemplary embodiment of target hardware (805) (for example, a computer system) for implementing the embodiments of FIG. 7. This target hardware comprises a video processing unit (VPU, 805), which can connect to the implant 810. The VPU may execute one or more instructions related to the implementation of FIG. 7, and as provided by an Operating System based on some executable program stored in a memory contained in the VPU 805. The VPU 805 may comprise a local interface that may comprise several elements such as controllers, buffers (caches), drivers, repeaters and receivers that are generally directed at providing address, control, and/or data connections between multiple elements of a processor based system (see FIG. 19). In some embodiments the processor may be fitted with some local memory (cache) where it can store some of the instructions to be performed for some added execution speed. The VPU 805 can process data from cameras, calculate a depth-based representation, and transmit necessary signals to the implant, where ultimately electrodes are activated thereby stimulating biological components that transmit visual information to the implantee. Preferably the VPU 805 includes an open multimedia applications platform (OMAP), field programmable gate array (FPGA) and double data rate (DDR) memory to help with disparity calculations.

As described above depth information is key to an effective obstacle avoidance system. In addition to stereo cameras for determining depth in near-real-time, time-of-flight or structured light may be used to calculate distance.

Time-of-flight data is derived from a range image camera system that determines distance based on the speed of light. The camera system measures the time-of-flight of light traveling between the subject for each point in the image and the camera. A time-of-flight camera uses scanner-less LIDAR which captures the entire scene in each light pulse of the laser. The difference between pulses determines distance information.

Structured light data is derived from projecting a known pattern, preferably a grid pattern on a scene. Distortions in the pattern, as viewed by the camera, provide depth information. The system will preferably use invisible grid patterns projected in infrared or ultraviolet light, which cannot be seen by human vision.

FIGS. 10-14 show various view of the preferred bilateral glasses for a visual prosthesis. A pair a cameras 705 are placed on the temple portion of the glasses 1005. The farther apart the two cameras 705 are placed, the greater the stereo effect and resulting ability to determine depth. The camera 705 may be a normal camera, time-of-of flight camera or structured light camera, in which case only a single camera is needed. An eye tracking camera 1004 is placed in front of an eye to track movement and select a subset of pixel from the cameras 2 based on the location of the gaze of the eye. It some cases a two eye tracking cameras or one that can be switch from side to side may be advantageous. One eye may not be move due damaged eye muscles or be block by the eyelid, such as by ptosis. Data from the cameras is sent to the VPU 805 to be processed and returned to the glasses 1005 for transmission over external coil 1017 to the visual prosthesis implant (shown in FIGS. 16 and 17). It should be noted that only one eye tracking camera 1004 is needed as both eyes move together. External coil 1017 may be placed in other location or may include multiple coils depending on the location of the implant or implants, as described elsewhere in this application. Specifically, the implant may also stimulate the visual cortex requiring the external coil 1017 to be on the back of the head.

Figure 15B:
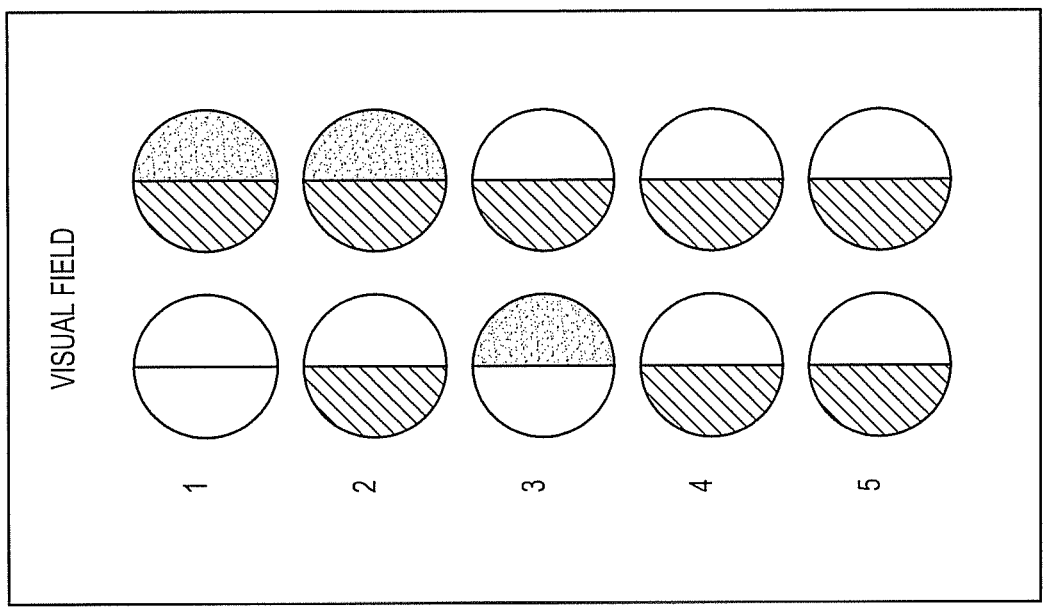
FIG. 15B how mapping changes along the pathways shown in FIG. 15A.
Figure 15A:
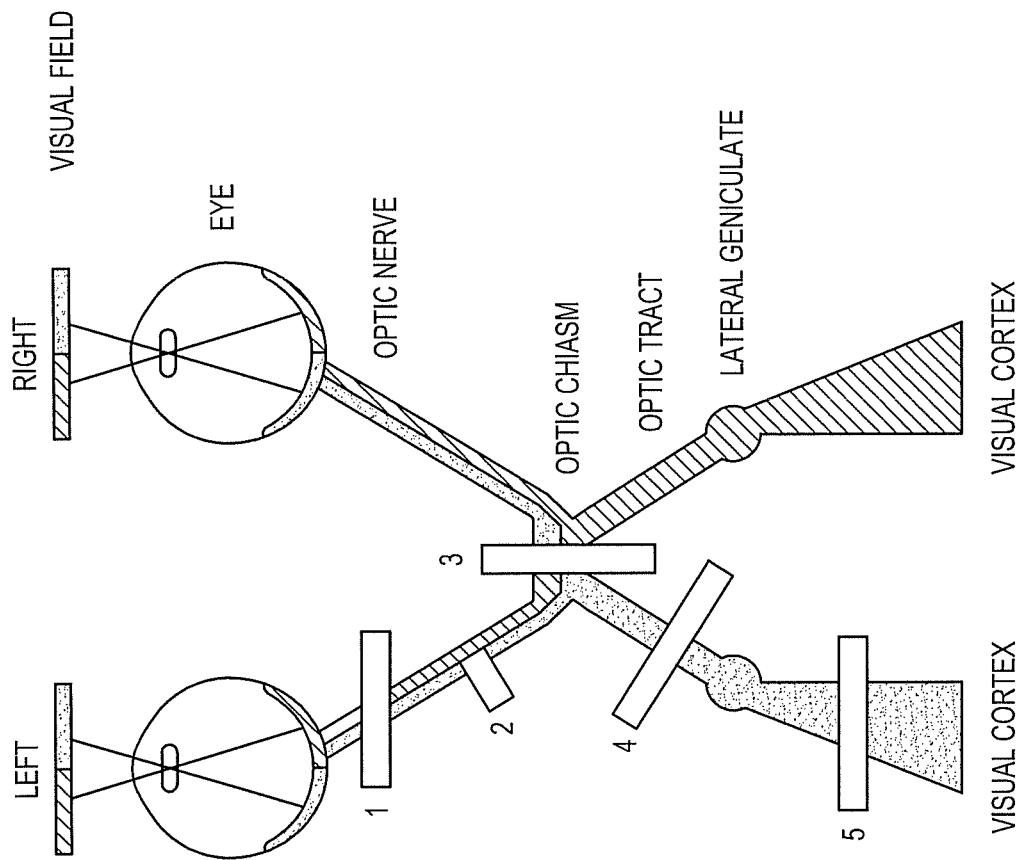
FIG. 15A shows the neural pathways of the visual field from the eyes to the brain.

FIGS. 15A and 15B show the complex mapping of visual information from the eyes to the brain. Two cameras may be preferentially placed on a frame like a glasses frame.

For a visual prosthesis, there is an additional advantage of two forward-facing cameras 705 when there is more than one implanted visual prosthesis or electrode array. There can be two electrode arrays that are either attached to a single implant or two separate implants which communicate to an external VPU 805 and glasses 1005. All the cameras 705 will connect to the VPU 805. The arrays may be placed on both retinas using two implants as those shown in FIGS. 16 and 17, or the two arrays may be placed on the two hemispheres of the visual cortex.

The disparity mode may be switchable. When not in disparity mode, the stereo cameras should map similar to the way natural vision is mapped. In this case, right and left refer to patient's right and left. If there is an electrode array in each eye, the video images from the right camera will preferentially be sent to the left portion of both electrode arrays and the video images from the left camera will be sent to the right portion of both electrode arrays. This is because the lens of a health eye inverts the image on the retina.

For electrode arrays in or on the visual cortex or LGN (lateral geniculate), the video images from the right camera will preferentially be sent to the electrode array on or in the left side of the brain. And the video images from the left camera will preferentially be sent to the electrode array on the right side of the brain.

For electrode arrays on or in the optic nerve distal to the optic chiasm, information from the left and right forward facing video cameras would likely be transmitted to stimulate both nerves. The specific mapping will be determined by experimentation—ie. The patient will be asked to locate the phosphene that resulted from a particular stimulation pattern on a particular electrode. Then, the right camera video images will be mapped to electrodes which corresponded to perceptions in the right visual field. Similarly, video images from the left camera will be mapped to electrodes which map to the left visual field.

Figure 16:
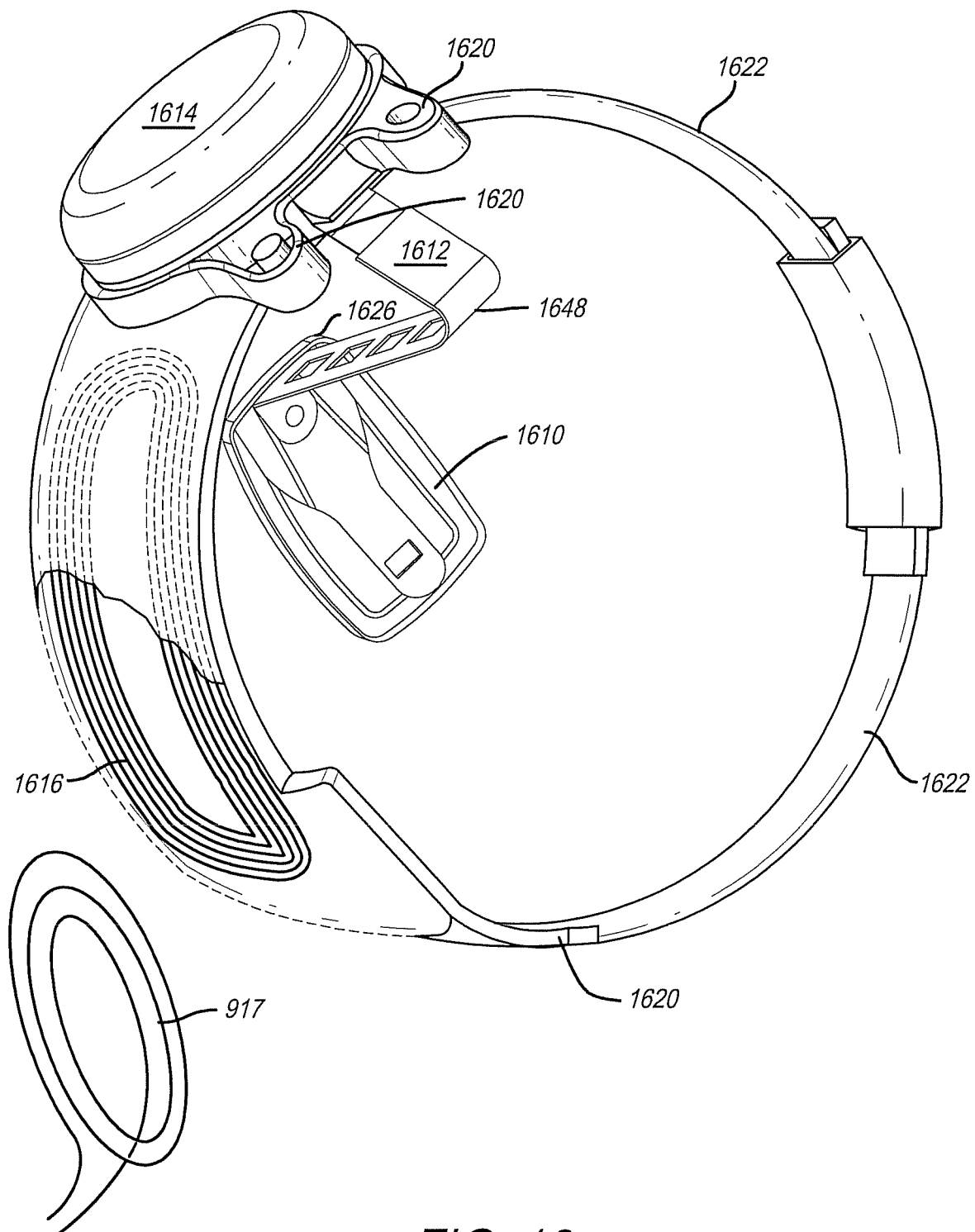
FIG. 16 is a perspective view of the implanted portion of the preferred visual prosthesis.
Figure 17:
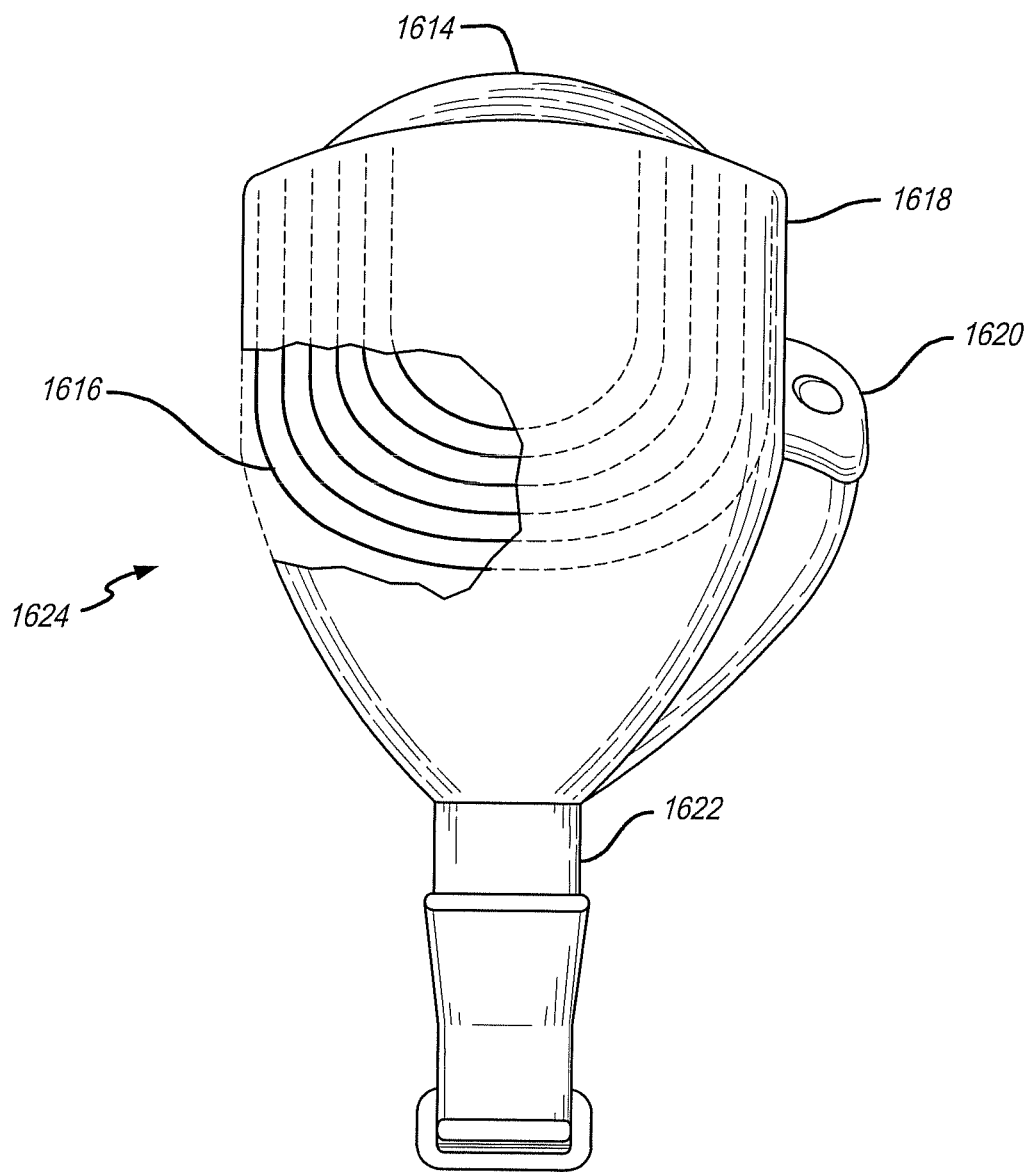
FIG. 17 is a side view of the implanted portion of the preferred visual prosthesis showing the strap fan tail in more detail.

FIGS. 16 and 17 present the general structure of the implanted portion of the visual prosthesis used in implementing the invention.

FIG. 16 shows a perspective view of the implanted portion of the preferred visual prosthesis. A flexible circuit includes a flexible circuit electrode array 1610 which is mounted by a retinal tack (not shown) or similar means to the epiretinal surface. The flexible circuit electrode array 1610 is electrically coupled by a flexible circuit cable 1612, which pierces the sclera and is electrically coupled to an electronics package 1614, external to the sclera.

The electronics package 1614 is electrically coupled to a secondary inductive coil 1616. Preferably the secondary inductive coil 1616 is made from wound wire. Alternatively, the secondary inductive coil 1616 may be made from a flexible circuit polymer sandwich with wire traces deposited between layers of flexible circuit polymer. The secondary inductive coil receives power and data from a primary inductive coil 917, which is external to the body. The electronics package 1614 and secondary inductive coil 1616 are held together by the molded body 1618. The molded body 1618 holds the electronics package 1614 and secondary inductive coil 1616 end to end. The secondary inductive coil 1616 is placed around the electronics package 1614 in the molded body 1618. The molded body 1618 holds the secondary inductive coil 1616 and electronics package 1614 in the end to end orientation and minimizes the thickness or height above the sclera of the entire device. The molded body 1618 may also include suture tabs 1620. The molded body 1618 narrows to form a strap 1622 which surrounds the sclera and holds the molded body 1618, secondary inductive coil 1616, and electronics package 1614 in place. The molded body 1618, suture tabs 1620 and strap 1622 are preferably an integrated unit made of silicone elastomer.

Silicone elastomer can be formed in a pre-curved shape to match the curvature of a typical sclera. However, silicone remains flexible enough to accommodate implantation and to adapt to variations in the curvature of an individual sclera. The secondary inductive coil 1616 and molded body 1618 are preferably oval shaped. A strap 1622 can better support an oval shaped coil. It should be noted that the entire implant is attached to and supported by the sclera. An eye moves constantly. The eye moves to scan a scene and also has a jitter motion to improve acuity. Even though such motion is useless in the blind, it often continues long after a person has lost their sight. By placing the device under the rectus muscles with the electronics package in an area of fatty tissue between the rectus muscles, eye motion does not cause any flexing which might fatigue, and eventually damage, the device.

FIG. 17 shows a side view of the implanted portion of the visual prosthesis, in particular, emphasizing the fan tail 1624. When implanting the visual prosthesis, it is necessary to pass the strap 1622 under the eye muscles to surround the sclera. The secondary inductive coil 1616 and molded body 1618 must also follow the strap 1622 under the lateral rectus muscle on the side of the sclera. The implanted portion of the visual prosthesis is very delicate. It is easy to tear the molded body 1618 or break wires in the secondary inductive coil 1616. In order to allow the molded body 1618 to slide smoothly under the lateral rectus muscle, the molded body 1618 is shaped in the form of a fan tail 1624 on the end opposite the electronics package 1614. The strap 1622 further includes a hook 1628 the aids the surgeon in passing the strap under the rectus muscles.

Figure 18:
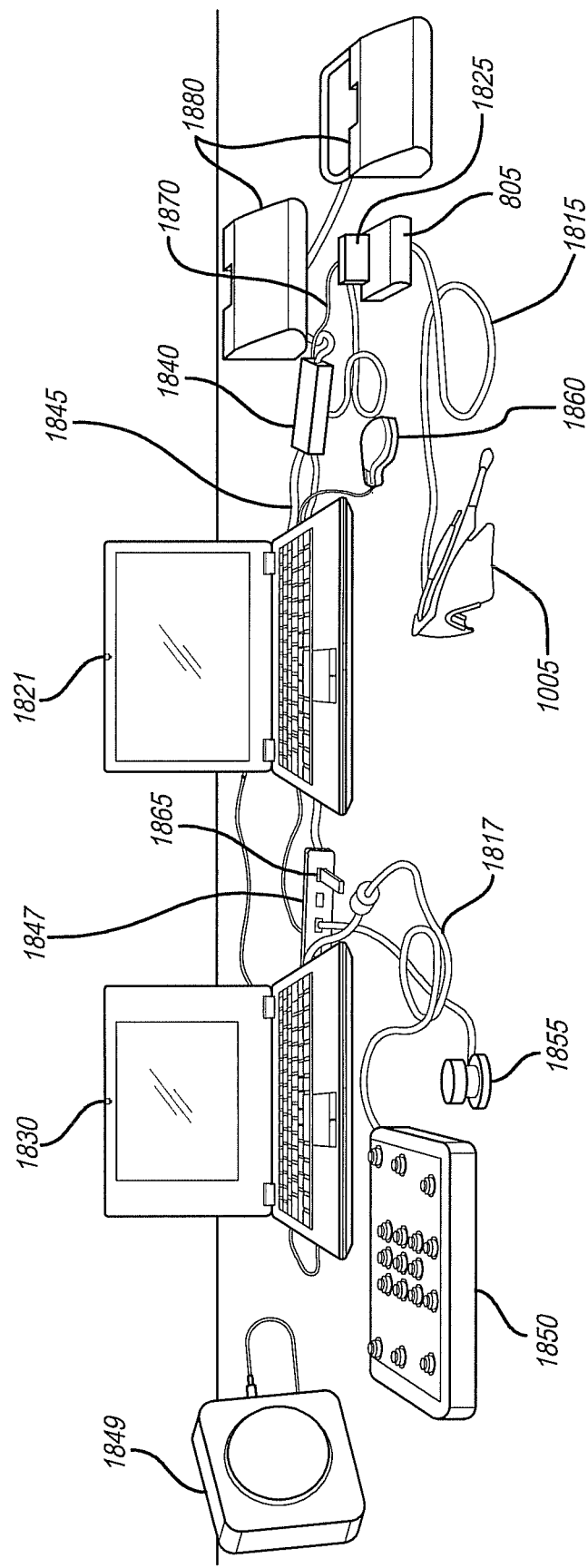
FIG. 18 shows the components of a visual prosthesis fitting system.

Referring to FIG. 18, a Fitting System (FS) may be used to configure and optimize a visual prosthesis. The Fitting System may comprise custom software with a graphical user interface (GUI) running on a dedicated laptop computer (1821). Within the Fitting System are modules for performing diagnostic checks of the implant, loading and executing video configuration files, viewing electrode voltage waveforms, and aiding in conducting psychophysical experiments. A video module can be used to download a video configuration file to a Video Processing Unit (VPU) (805) and store it in non-volatile memory to control various aspects of video configuration, e.g. the spatial relationship between the video input and the electrodes. The software can also load a previously used video configuration file from the VPU (805) for adjustment.

The Fitting System can be connected to the Psychophysical Test System (PTS), located for example on a dedicated laptop (1821), in order to run psychophysical experiments. In psychophysics mode, the Fitting System enables individual electrode control, permitting clinicians to construct test stimuli with control over current amplitude, pulse-width, and frequency of the stimulation. In addition, the psychophysics module allows the clinician to record subject responses. The PTS may include a collection of standard psychophysics experiments developed using for example MATLAB (MathWorks) software and other tools to allow the clinicians to develop customized psychophysics experiment scripts.

Any time stimulation is sent to the VPU (805), the stimulation parameters are checked to ensure that maximum charge per phase limits, charge balance, and power limitations are met before the test stimuli are sent to the VPU (805) to make certain that stimulation is safe.

Using the psychophysics module, important perceptual parameters such as perceptual threshold, maximum comfort level, and spatial location of percepts may be reliably measured.

Based on these perceptual parameters, the fitting software enables custom configuration of the transformation between video image and spatio-temporal electrode stimulation parameters in an effort to optimize the effectiveness of the visual prosthesis for each subject.

The Fitting System laptop (1821) is connected to the VPU (805) using an optically isolated serial connection adapter (1840). Because it is optically isolated, the serial connection adapter (1840) assures that no electric leakage current can flow from the Fitting System laptop (1821).

As shown in FIG. 18, the following components may be used with the Fitting System according to the present disclosure. A Video Processing Unit (VPU) (805) for the subject being tested, a Charged Battery (1825) for VPU (805), Glasses (1005), a Fitting System (FS) Laptop (1821), a Psychophysical Test System (PTS) Laptop (1830), a PTS CD (not shown), a Communication Adapter (CA) (1840), a USB Drive (Security) (not shown), a USB Drive (Transfer) (not shown), a USB Drive (Video Settings) (not shown), a Patient Input Device (RF Tablet) (1850), a further Patient Input Device (Jog Dial) (1855), Glasses Cable (1815), CA-VPU Cable (1870), CFS-CA Cable (1845), CFS-PTS Cable (1846), Four (4) Port USB Hub (1847), Mouse (1860), LED Test Array (1880), Archival USB Drive (1849), an Isolation Transformer (not shown), adapter cables (not shown), and an External Monitor (not shown).

The external components of the Fitting System according to the present disclosure may be configured as follows. The battery (1825) is connected with the VPU (805). The PTS Laptop (1830) is connected to FS Laptop (1821) using the CFS-PTS Cable (1846). The PTS Laptop (1830) and FS Laptop (1821) are plugged into the Isolation Transformer (not shown) using the Adapter Cables (not shown). The Isolation Transformer is plugged into the wall outlet. The four (4) Port USB Hub (1847) is connected to the FS laptop (1821) at the USB port. The mouse (1860) and the two Patient Input Devices (1850) and (1855) are connected to four (4) Port USB Hubs (1847). The FS laptop (1821) is connected to the Communication Adapter (CA) (1840) using the CFS-CA Cable (1845). The CA (1840) is connected to the VPU (805) using the CA-VPU Cable (1870). The Glasses (1005) are connected to the VPU (805) using the Glasses Cable (1815).

As discussed above, the VPU 805 processes the image from the camera 705 and transforms the image into electrical stimulation patterns for the retinal stimulation system. Filters such as edge detection filters may be applied to the electrical stimulation patterns for example by the VPU 805 to generate, for example, a stimulation pattern based on filtered video data that the VPU 805 turns into stimulation data for the retinal stimulation system. The images may then be reduced in resolution using a downscaling filter. In one exemplary embodiment, the resolution of the image may be reduced to match the number of electrodes in the electrode array 1610 of the retinal stimulation system. That is, if the electrode array has, for example, sixty electrodes, the image may be reduced to a sixty channel resolution. After the reduction in resolution, the image is mapped to stimulation intensity using for example a look-up table that has been derived from testing of individual subjects. Then, the VPU 805 transmits the stimulation parameters via forward telemetry to the retinal stimulation system in frames that may employ a cyclic redundancy check (CRC) error detection scheme.

One exemplary embodiment of the VPU 805 is shown in FIG. 19. The VPU 805 may comprise: a Power Supply, a Distribution and Monitoring Circuit (PSDM) 1905, a Reset Circuit 1910, a System Main Clock (SMC) source (not shown), a Video Preprocessor Clock (VPC) source (not shown), a Digital Signal Processor (DSP) 1920, Video Preprocessor Data Interface 1925, a Video Preprocessor 1975, an I²C Protocol Controller 1030, a Complex Programmable Logic device (CPLD) (not shown), a Forward Telemetry Controller (FTC) 1935, a Back Telemetry Controller (BTC) 1940, Input/Output Ports 1945, Memory Devices like a Parallel Flash Memory (PFM) 1050 and a Serial Flash Memory (SFM) 1955, a Real Time Clock 1960, an RF Voltage and Current Monitoring Circuit (VIMC) (not shown), a speaker and/or a buzzer, an RF receiver 1965, and an RF transmitter 1970.

The Power Supply, Distribution and Monitoring Circuit (PSDM) 1905 may regulate a variable battery voltage to several stable voltages that apply to components of the VPU 805. The Power Supply, Distribution and Monitoring Circuit (PSDM) 1005 may also provide low battery monitoring and depleted battery system cutoff. The Reset Circuit 1010 may have reset inputs 1911 that are able to invoke system level rest. For example, the reset inputs 1911 may be from a manual push-button reset, a watchdog timer expiration, and/or firmware based shutdown. The System Main Clock (SMC) source is a clock source for DSP 1920 and CPLD. The Video Preprocessor Clock (VPC) source is a clock source for the Video Processor. The DSP 1920 may act as the central processing unit of the VPU 805. The DSP 1920 may communicate with the rest of the components of the VPU 805 through parallel and serial interfaces. The Video Processor 1975 may convert the NTSC signal from the camera 13 into a down-scaled resolution digital image format. The Video Processor 1975 may comprise a video decoder (not shown) for converting the NTSC signal into high-resolution digitized image and a video scaler (not shown) for scaling down the high-resolution digitized image from the video decoder to an intermediate digitized image resolution. The video decoder may be composed of an Analog Input Processing, Chrominance and Luminance Processing and Brightness Contrast and Saturation (BSC) Control circuits. The video scaler may be composed of Acquisition control, Pre-scaler, BSC-control, Line Buffer and Output Interface. The I²C Protocol Controller 1930 may serve as a link between the DSP 1920 and the I²C bus. The I²C Protocol Controller 1930 may be able to convert the parallel bus interface of the DSP 1920 to the I²C protocol bus or vice versa. The I²C Protocol Controller 1930 may also be connected to the Video Processor 1975 and the Real Time Clock 1960. The VPDI 1925 may contain a tri-state machine to shift video data from Video Preprocessor 1975 to the DSP 1920. The Forward Telemetry Controller (FTC) 1935 packs 1924 bits of forward telemetry data into a forward telemetry frame. The FTC 1935 retrieves the forward telemetry data from the DSP 1920 and converts the data from logic level to biphase marked data. The Back Telemetry Controller (BTC) 1940 retrieves the biphase marked data from the RF receiver 1965, decodes it, and generates the BFSR, BCLKR and BDR for the DSP 1920. The Input/Output Ports 1945 provide expanded JO functions to access the CPLD on-chip and off-chip devices. The Parallel Flash Memory (PFM) 1950 may be used to store executable code and the Serial Flash Memory (SFM) 1955 may provide Serial Port Interface (SPI) for data storage. The VIMC may be used to sample and monitor RF transmitter 1970 current and voltage in order to monitor the integrity status of the retinal stimulation system.

The methods and systems described in the present disclosure may be implemented in hardware, software, firmware or any combination thereof. Features described as blocks, modules or components may be implemented together (for example, in a logic device such as an integrated logic device) or separately (for example, as separate connected logic devices).

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a", "an", and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

What is claimed is:

1. A visual prosthesis comprising:
   stereo cameras sending visual information, and mounted on a pair of glasses;
   an accelerometer detecting acceleration and movement of the glasses, and generating movement data;
   a video processor deriving depth information from the video information and combining the depth information with the video information to provide indicia of depth within stimulation patterns, and combining depth information with movement data to correct the stereo cameras to horizontal to remove a ground plane;
   a transmitter receiving the stimulation patterns and transmitting the stimulation patterns; and
   an implantable neurostimulator receiving the stimulation patterns from the transmitter, and stimulating neural tissue according to the stimulation patterns.

2. The visual prosthesis according to claim 1, wherein the source of depth information includes a time-of-flight camera.

3. The visual prosthesis according to claim 1, wherein the source of depth information includes a structured light camera.

4. The visual prosthesis according to claim 1, wherein the video processor is configured to detect obstacles based on the visual information and the depth information, to remove a ground plane, to calculate a map of pixels representing the obstacles, and to alter the stimulation patterns based on the map of pixels.

5. The visual prosthesis according to claim 1, wherein the stereo cameras are configured to generate captured images; and the video processor is configured to:
- synchronize the captured images;
- calculate a disparity map between the captured images;
- detect a ground plane based on the disparity map;
- generate a processed image representative of a view in front of the system user, based on the captured images and the disparity map;
- remove the ground plane from the processed image;
- generate a map of pixels representing the obstacles; and
- alter the stimulation patterns based on the map of pixels.

6. The visual prosthesis according to claim 1, wherein the stereo cameras are mounted in temple portions of the glasses.

7. The visual prosthesis according to claim 1, further comprising an eye tracking camera mounted on the glasses.

8. The visual prosthesis according to claim 1, wherein the video processor adds greater intensity to closer objects and less intensity to more distant objects.

\* \* \* \* \*